United States Patent
Bloder et al.

(10) Patent No.: US 6,874,351 B2
(45) Date of Patent: Apr. 5, 2005

(54) DETERMINING THE QUANTITIES OF GASES DISSOLVED IN A LIQUID

(75) Inventors: Josef Bloder, Gleisdorf (AT); Josef Gautsch, Graz (AT); Klauss Germann, Graz (AT); Gerhard Murer, Graz (AT)

(73) Assignee: Anton Paar GmbH, Graz (AT)

(*) Notice: Subject to any disclaimer, the term of this patent is extended or adjusted under 35 U.S.C. 154(b) by 0 days.

(21) Appl. No.: 10/104,485

(22) Filed: Mar. 22, 2002

(65) Prior Publication Data

US 2003/0029228 A1 Feb. 13, 2003

(30) Foreign Application Priority Data

Mar. 23, 2001 (AT) ........................................ A 472/2001

(51) Int. Cl.[7] ................................................. G01N 7/00
(52) U.S. Cl. .................... 73/19.05; 73/19.06; 73/19.02; 73/19.03
(58) Field of Search ............................ 73/19.05, 19.06, 73/19.02, 19.03

(56) References Cited

U.S. PATENT DOCUMENTS

| | | | | |
|---|---|---|---|---|
| 4,276,769 A | * | 7/1981 | Wieland et al. ............. | 73/19.05 |
| 4,563,892 A | * | 1/1986 | D'Aoust .................... | 73/19.05 |
| 4,745,794 A | * | 5/1988 | Steichen et al. ............ | 73/19.03 |
| 5,426,593 A | * | 6/1995 | Seiden et al. ............... | 73/19.01 |
| 6,192,737 B1 | * | 2/2001 | Ohlrogge et al. ........... | 73/19.06 |
| 6,277,329 B1 | * | 8/2001 | Evans ........................ | 73/19.12 |

* cited by examiner

Primary Examiner—Hezron Williams
Assistant Examiner—André K. Jackson
(74) Attorney, Agent, or Firm—Townsend and Townsend and Crew, LLP

(57) ABSTRACT

A method for determining the content quantities, solubilities and/or saturation pressures of gases dissolved in a liquid, which is characterized in that in order selectively to determine the individual content quantities of at least two gases dissolved in a liquid sample, more particularly carbon dioxide, nitrogen and/or oxygen, and/or the solubilities or saturation pressures thereof, the volume of at least one measuring chamber filled with the liquid for testing is increased the volume of at least two steps by volume increase factors differing one from another, each having numerical values greater than 1, in that, after each of the volume increase steps, the equilibrium pressure established in the measuring chamber is ascertained, and in that, on the basis of the at least two measured pressure values obtained in this way, the content quantities of the individual gases dissolved in the liquid, and/or the solubility or saturation pressure thereof, are calculated individually. Also disclosed are several variants of a device for implementing the analysis method.

43 Claims, 4 Drawing Sheets

DETERMINING THE QUANTITIES OF GASES DISSOLVED IN A LIQUID

BACKGROUND OF THE INVENTION

Figure 1:
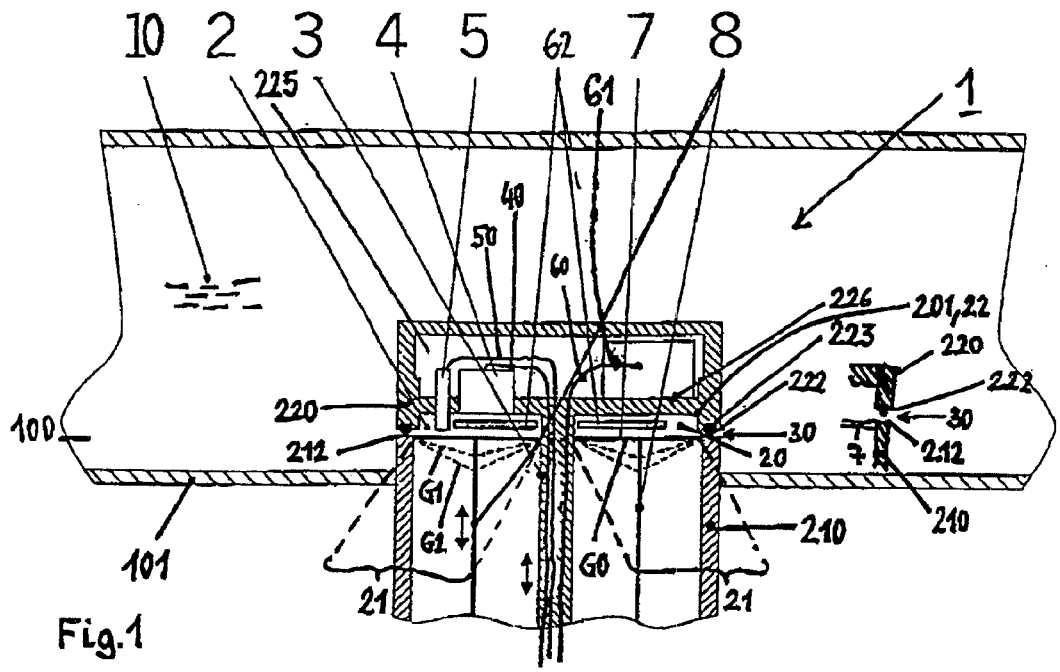

The present invention relates to a method and also a device for selectively determining the content quantities of gases, such as carbon dioxide, nitrogen and/or oxygen, for example, dissolved in liquids, such as beverages, and also for ascertaining the solubility (solubilities) and/or saturation pressure(s) thereof in the liquids.

The main emphasis of the invention is the determination of the content quantities of gases dissolving in liquids or dissolved in the same in fairly large quantities. However, as well as the content quantities of more than one gas dissolved in a liquid, which is of prime interest here, it should also be possible to determine the solubility (solubilities) and/or the saturation pressure(s) of an individual gas or of several gases in the liquid.

Constituting a further essential subject of the invention is a device in the form of various design variants for determining content quantities, solubility (solubilities) and/or saturation pressure(s) of at least one gas, but preferably at least two or more gases, in a liquid containing the gas or gases dissolved therein, the main emphasis being the implementation of the new determination method just referred to.

A considerable number of often quite different methods and devices for determining the content quantities of gases dissolved in liquids, such as carbon dioxide in particular, have become well known and also commercially available. Some of these known methods and devices are in principle also suitable for determining other gases, such as oxygen and/or nitrogen in particular, dissolved in liquids such as beverages, for example. The characteristic features of these will be briefly described below:

a) Pressure and temperature measurement in a sealed measuring chamber expanded once:

A representative sample of the liquid for measuring is introduced into a measuring chamber. Where measurements are performed on casks of beverages, the whole cask often serves as the measuring chamber. After the measuring chamber has been closed, the liquid sample to be analyzed is expanded by increasing the volume of the measuring chamber, e.g. by means of a piston-type injector fitted fluid-tight to the chamber, or, where measuring is being implemented in the beverage cask, by means of a short release of pressure. The pressure established after the expansion and the sample temperature are then measured. The carbon dioxide content is then calculated from these in accordance with Henry's law. Other gases dissolved in the sample liquid, such as oxygen and nitrogen in particular, affect the ascertained carbon dioxide content. Commercially available devices differ from one another by, among other things, the method of sampling, the shape of the measuring chamber, and by differing measures for the accelerated establishment of equilibrium pressure after the expansion or for extrapolating the equilibrium pressure.

b) Measurement in a liquid-free measuring chamber separated by a gas-permeable membrane:

A membrane substantially permeable only to carbon dioxide separates a measuring chamber from the sample liquid. The measuring chamber is periodically evacuated or flushed with a reference gas. The carbon dioxide content or its variation over time in the measuring chamber is then ascertained by measuring pressure, thermal conductivity or infrared absorption and in addition temperature, and from these the carbon dioxide content of the liquid is then calculated.

c) Measurement in a liquid-filled measuring chamber separated by a gas-permeable membrane:

A membrane substantially permeable only to carbon dioxide separates a measuring chamber filled with a suitable liquid from the liquid for analysis. As a result of absorbing the carbon dioxide permeating through the membrane, the liquid in the measuring chamber changes, e.g. in its pH value, which is measured together with the temperature, from which the carbon dioxide content of the liquid to be analyzed for the carbon dioxide content can then be calculated.

d) Direct infrared absorption measurement:

By means of infrared absorption measurements, usually in the mid infrared range, performed on the liquid to be analyzed, or sample liquid, the carbon dioxide content in the liquid is directly determined.

e) Wet chemical analysis:

In a defined sample volume, by means of the addition of appropriate chemicals the dissolved carbon dioxide is absorbed, separated out, and determined gravimetrically or titrimetrically.

In d) and e) the carbon dioxide content is directly determined; in a)–c) the saturation pressure of the carbon dioxide in the liquid for analysis is primarily ascertained. With the solubility of the carbon dioxide in the liquid for analysis taken as known, assumed or only estimated, the carbon dioxide content of this liquid is calculated from the saturation pressure ascertained directly or indirectly. Since in practice the solubility of a gas in an aqueous solution other than pure water is always known only approximately at most, a problem arises from this if the results of different methods are compared with one another.

The present invention is based in particular on the group of methods and devices described above under a) which are based on pressure and temperature measurements in a sealed measuring chamber which has been expanded in a defined manner in only one step.

SUMMARY OF THE INVENTION

The subject of the present invention is a new method for determining the content quantities of gases dissolved in a liquid, preferably a beverage, wherein, after a measuring chamber equipped at least with a pressure-measuring sensor has been filled completely with the liquid to be tested for its gas content (the "sample liquid"), and after the measuring chamber has been closed fluid-tight, the volume thereof is increased—starting from a standard volume—by a predetermined factor, and the equilibrium pressure established thereafter in the measuring chamber is ascertained, and—based on the measured pressure value obtained in this way—the gas content of the liquid for analysis is calculated. This method involves:

selectively determining the individual content quantities of at least two or more gases, more particularly carbon dioxide, nitrogen and/or oxygen, which differ from one another in their solubilities and are dissolved in the sample liquid, and/or the solubilities and/or the saturation pressures of the gases, in at least two or more steps corresponding at least to the number of gases dissolved in the liquid and to be tested for their content quantities, increasing the volume of at least one measuring chamber filled with the sample liquid, starting from the standard measuring chamber volume, by volume increase factors differing from one another—each having numerical values greater than 1, after each of the volume increase steps, ascertaining the equilibrium pressure established in each case in the measuring chamber, and on the basis and with the inclusion of the at least two measured pressure values obtained in this way, individually calculating the content quantities of the individual gases contained or dissolved in the liquid, and optionally the solubility and/or the saturation pressure of at least one of the gases in the sample liquid.

The new method has the following new features which are extremely important for commercial application, and offers in particular the following advantages:

The effect of other gases dissolved in the sample liquid on the ascertained gas content, i.e. the carbon dioxide content, for example, is minimized. In preferred embodiments the effect of each of the other dissolved gases can be eliminated, so that the content quantities of other gases dissolved in the sample liquid, such as oxygen and nitrogen, can also be determined.

The actual solubilities and/or saturation pressures of the individual gases dissolved in the sample liquid may additionally be ascertained and thus the content quantities of these gases can be determined exactly, although their solubility in the actual sample liquid, other than pure water, is not known.

The method according to the invention is characterized, amongst other things, in particular in that, for example, the effect of other dissolved gases, i.e. other than $CO_2$, for instance, on the carbon dioxide content of the sample liquid ascertained in the particular case can be eliminated, and in that optionally the content quantities of the other gases dissolved in the sample liquid, and also the actual solubilities of each individual one of these gases in the sample liquid; can be determined as well.

Along with the main component, carbon dioxide, already repeatedly mentioned above, oxygen and nitrogen are the "other" important gases dissolved in beverages or similar liquids to which gas content measurements are applicable. The solubilities of carbon dioxide, oxygen and nitrogen in aqueous solutions differ considerably from one another.

If the sample of liquid, abbreviated to sample liquid, is expanded in the sealed measuring chamber, a liquid and a gas phase form from the original single liquid phase in which all the gases are dissolved. Because of the very different solubilities of the gases in the sample liquid, the proportion of the partial pressures of the individual gases in the gas phase differs substantially from the proportion of the saturation pressures of the dissolved gases in the original, i.e. pre-expansion, sample liquid. The general principle is that the lower the solubility of a gas in a liquid is, the more the partial pressure of the gas dissolved in the liquid decreases when the volume is increased.

Thus in the method according to the invention— specifically to determine the content quantities of at least two gases dissolved in the sample liquid—at least two or more than two volume increase steps are implemented in each case. After each of these volume increase steps, the equilibrium pressure then established and advantageously also the temperature prevailing at the time are each measured. From the values ascertained are calculated the content quantities and, if required, also the solubilities and/or saturation pressures of the individual gas components differing from each other in their individual solubilities.

The basic algorithms used within the scope of the present invention—to calculate content quantities, and also solubilities and saturation pressures, and thus for simpler cases—are explained with the aid of the following calculation example which describes in general terms and in actual numbers the method of calculation—representing a component part of the invention:

The following is a calculation example for a beverage, such as beer for example, which exists as a liquid phase enriched by carbon dioxide and nitrogen:

Solubilities L at a specific measuring temperature: $L(CO_2)=1.058$ bar$^{-1}$ $L(N_2)=0.017$ bar$^{-1}$ Saturation pressures: $pCO_2=2.50$ bar $pN_2=2.00$ bar As a result of a volume increase, on the basis of Henry's and Boyle's laws the following partial pressures occur in the gas phase:

$p' = p/(1 + k/(L*p_s))$  
p'  partial pressure of a gas after the measuring chamber volume increase  
p   original saturation pressure of the gas in the liquid  
k   volume increase factor  
L   solubility of the gas in the sample liquid  
$p_s$  standard pressure (1 bar)

Volume increase of 3% and 10% respectively:

$k_1=0.03$ $k_2=0.10$ $p'CO_2=2.431$ bar $p'CO_2=2.284$ bar $p'N_2=0.723$ bar $p'N_2=0.291$ bar Measured pressure ($=p'CO_2+p'N_2$):

$p_1=3.154$ bar $p_2=2.575$ bar

From the equilibrium pressures $p_1$ and $p_2$ measured after the two volume increases $k_1$ and $k_2$ to be implemented according to the invention, the original saturation pressures pX and pY of two dissolved gases with known solubilities L(X) and L(Y) are calculated with the aid of the following linear equation system:

$p_1=pX/(1+k_1/(L(X)*p_s))+pY/(1+k_1/(L(Y)*p_s))$ $p_2=pX/(1+k_2/(L(X)*p_s))+pY/(1+k_2/(L(Y)*p_s))$

This equation system is to be solved according to pX and pY.

When the numerical values $L(CO_2)=1.058$, $L(N_2)=0.017$, $k_1=0.03$, $k_2=0.10$, $p_s=1$ given in this example are used and the equation system is solved according to pX ($=pCO_2$) and pY ($=pN_2$), the following equations result for $pCO_2$ and $pN_2$:

$pCO_2=-0.7681*p_1+1.9120*p_2$ (=2.50 bar for $p_1=3.154$ and $p_2=2.575$ bar)

$pN_2=4.8297*p_1-5.1405*p_2$ (=2.00 bar for $p_1=3.154$ and $p_2=2.575$ bar)

Multiplying the calculated saturation pressures $pCO_2$ and $pN_2$ by the respective gas solubility $L(CO_2)$ or $L(N_2)$ produces the sought gas contents in the sample liquid.

With the units selected here, the gas contents are produced as "volume of dissolved gas in the standard state per volume of liquid". This industrially standard unit for the gas content may be converted by means of simple conversion factors into other units, such as "g/L", for example.

Optionally the above calculation may be amplified by a correction which eliminates the temperature-dependent vapor pressure of the liquid sample components from the measured pressure values, but this is not set out in detail here.

Using the two-step or multiple-step method according to the invention, as well as the saturation pressures, the solubilities of carbon dioxide and/or other gases dissolved in the sample liquid may also be determined, as already mentioned quite briefly in the introduction. This is particularly important when the content quantities of several gases dissolved in the sample liquid are to be determined and the solubilities of the individual dissolved gases to be determined in the actual liquid itself are not precisely known. This is very often the case as the rest of the composition of the sample liquid has a strong effect on the solubilities of the gases dissolved therein; e.g. the solubilities of the aforementioned gases in a fruit acid drink are completely different from those of the same gases in pure water.

In principle it follows that for every unknown quantity—whether this is the gas content and/or the solubility and/or the saturation pressure of individual gas components in the liquid—at least one additional volume increase with subsequent determination of the equilibrium pressure are required for each in any case.

If there is only one gas dissolved in the sample liquid, the saturation pressure and solubility may be determined as follows from the pressures $p_1$ and $p_2$ established and measured after two volume increases $k_1$ and $k_2$:

$$L(X)=(p_1*k_2-p_2*k_2)/(p_2-p_1)/p_s$$

$$pX=p_1*(1+k_1)/(L(X))*p_s$$

With the aid of the data for $CO_2$ from the previous calculation example, the following is obtained:

$$L(CO_2)=(2.431*0.03-2.284*0.10)/(2.284-2.431)=1.058 \text{ bar}^{-1}$$

$$pCO_2=2.431*(1+0.03/1.058)=2.50 \text{ bar}$$

Where there are several gases dissolved, a corresponding number of volume increase steps and correspondingly more extensive calculation methods are necessary. If more than one gas is dissolved and the solubilities of individual gases are also to be ascertained, non-linear higher-order equation systems result. Their solution is typically achieved iteratively, starting from precise estimated values for the unknown gas solubilities which are as realistic as possible.

If a gas dissolved in the sample liquid is present in a much greater quantity than all the other gases dissolved therein, and if the solubilities of the other gases are substantially lower and possibly even alike, these other gases may be treated as a single gas component. This is advantageous if, for instance, as well as the carbon dioxide content of a sample, only the air content, for example, is to be determined or if only the effect of all the other dissolved gases on the ascertained carbon dioxide content is to be eliminated. In this case it is possible to use in the equation system for the "hypothetical" solubility of the "other" dissolved gases a weighted mean value of their actual solubilities.

If, for example, only the content and the solubility of $CO_2$ as the important main component are sought and oxygen and nitrogen are only dissolved to a minor degree, by means of two accordingly large volume increases, e.g. by 10% and by 20%, the effect of oxygen and nitrogen can also be suppressed to the extent that it can be disregarded and no specific volume increase steps are necessary in order to take it into consideration. Use is made here of the fact that, because of the very low solubilities of oxygen and nitrogen, their partial pressures in the gas phase decrease vary markedly as a result of an increased volume increase—as just described—and are no longer significant.

With regard to the factors of the measuring chamber volume increases advantageously to be observed within the scope of the present invention, such volume increase factors of between 1.005 and 1.75 have proved advantageous for extreme cases. In some cases these factors may range from 1.01 to 1.50 and in most conventional routine analyses where there is no specific suppression of the effect of other gas components present in small quantities in the sample liquid, volume increase factors of between 1.03 and 1.15, preferably 1.03 to 1.10, have proved successful.

Since the solubility of gases in liquids generally is dependent to a considerable extent on the temperature, apart from routine measurements with temperature conditions remaining virtually constant, it is preferable to measure the temperature of the sample liquid and include it—if necessary—in the calculations.

If the procedure involves only one measuring chamber in which the preferably at least two volume increase steps are performed one after the other, constancy of the measuring conditions, desired per se, is ensured in a simple manner.

It has also proved advantageous to employ a variant of the measuring method in which it is provided that, preferably at the same time, two measuring chambers located slightly apart or adjacent to one another are filled with sample liquid and, again preferably at the same time, the volume increase steps, which differ from each other, are then implemented.

To achieve the quickest possible establishment of the equilibrium pressures, it is preferred, particularly in the case where a single measuring chamber is used, to implement the volume increase steps occurring in chronological succession with gradually increasing volume increase factors in each case.

If—as already indicated above—only a limited, low number of gases as main components dissolved in the sample liquid or only one gas is determined and the effect of the other gas components dissolved in the liquid are suppressed, it has proved advantageous substantially to increase the volume changes in the volume increase steps. If, as already mentioned, these amount to about 1% to 10% in routine analyses, it is advantageous in this design variant, by disregarding of the gases dissolved in small quantities in the sample liquid, to increase the volume increase in at least one of the volume increase steps by a percentage of at least 20%.

As far as the disregarding referred to above of less significant or unimportant gas components in the sample liquid is concerned, it may be advantageous with respect to these other components, such as air, for example, to assume a "mean" solubility or a mean saturation pressure for them.

With respect to the way in which the measuring chamber volume increase is brought about, it has already been set out with reference to the prior art that a sort of piston-type injector is used for this, it being important here that fluid-tightness is maintained in every case.

In the context of the development work for the invention, it has proved advantageous with regard to the fluid-sealing, mechanical effort, and costs involved to use, instead of a displaceable piston, a defined and reproducibly deformable membrane, made of an elastomer, for example.

It should be mentioned at this point that a method of this kind, operating with a volume-increasing membrane, is new as such, and that the use of such a membrane is therefore not limited to a method with a two-step volume increase, but that such a measuring chamber with a membrane is entirely applicable as well to the gas content determining method according to the prior art discussed in the introduction under a).

It may be particularly advantageous within the scope of the method according to the invention to augment the equilibrium pressure measurements by the addition of selective gas sensors to determine the content of individual gases dissolved in the liquid, and let the results relating thereto possibly also be included in the calculation of the content quantities of the other gases.

Hitherto none of the instruments of the prior art mentioned in the introduction under a) could be described as really satisfactory as far as establishing the equilibrium gas pressure as quickly and reproducibly as possible after each volume increase step is concerned. In the course of the development of the method according to the invention it has become apparent that generating cavitation in the sample liquid causes the establishing of equilibrium pressure to take place very quickly.

Various methods may be used to achieve the cavitation effect in the sample liquid located in the measuring chamber.

Here too it should be emphasized that this new method for accelerating the establishing of the equilibrium pressure after each measuring chamber volume increase has taken place is not limited to a two-step volume increase method, but may also be used in the same way in the one-step method according to the prior art.

It is especially preferred, particularly with regard to generating cavitation effects in the sample liquid, to bring about the desired establishment of the equilibrium pressure in the measuring chamber by means of a power-regulated ultrasonic transducer.

With regard to the introduction of ultrasonic energy, it is advantageous to adapt the amount thereof to the particular liquid to be analyzed for its gas contents, the inclusion of the change over time of the pressure occurring and measured in the measuring chamber after the ultrasonic transducer has been switched off being advantageous as a regulating variable for the ultrasonic power to be introduced into the sample liquid.

This method variant too may be used both for the one-step volume increase method already previously known and also for the multiple-step volume increase method according to the invention.

Another essential subject of the present invention is constituted by a new device for selectively determining the content quantity (quantities) and/or solubility (solubilities) and/or saturation pressure(s) of at least one gas dissolved in a liquid, preferably a beverage, wherein, after a measuring chamber equipped at least with a pressure-measuring sensor has been filled completely with the liquid to be tested for its gas content (the "sample liquid"), and, after the measuring chamber has been closed fluid-tight, the volume thereof is increased at least once by a predetermined volume increase factor and the equilibrium pressure established thereafter in the measuring chamber is ascertained, and—based on the measured pressure value obtained in this way—the gas content of the liquid for analysis and/or the solubility of the gas in the liquid is calculated, in particular for the implementation of the method according to the invention previously described in its various embodiments.

The new device is characterized in a first preferred embodiment in that it has a fluid-tight measuring chamber which may be filled completely with the sample liquid and closed fluid-tight, comprising at least one partial region of the boundary or wall of its interior space, which partial region is provided for changing the volume of the interior space thereof, is variable in its position and/or surface geometry—while fully retaining the fluid-tightness—and is preferably formed by a membrane, which partial region—starting from a standard position and/or standard geometry—is movable into, and/or deformable to, at least one defined location position and/or surface geometry—producing an increase in the volume of the measuring chamber interior space corresponding in each case to a freely selectable and adjustable volume increase factor.

If at least two gases dissolved in a liquid are to be selectively determined, as provided in particular in accordance with the method according to the invention previously described in its variants, an embodiment of the device which includes a partial region of the interior space boundary or wall of the measuring chamber which is variable in its position and/or surface geometry and is preferably formed by a membrane, is movable into, and/or deformable to, at least two mutually differing defined location positions and/or surface geometries, thereby producing increases in the volume of the measuring chamber interior space corresponding in each case to a freely selectable and adjustable volume increase factor.

Another variant of the device for the purpose previously described is characterized in that it has at least two measuring chambers, preferably of identical design, adapted for filling completely with the sample liquid and closable fluid-tight, each comprising at least one partial region of the boundary or wall of its respective interior space, which partial region is provided in each case for changing the volume of the interior space thereof, is variable in its position and/or surface geometry while fully retaining the fluid tightness, and is preferably formed by a membrane, each of which partial regions is movable into, and/or deformable to, at least one defined location position and/or surface geometry respectively—producing an increase in the volume of the measuring chamber interior space corresponding in each case to a freely selectable and adjustable volume increase factor.

The advantage of this second device variant according to the invention is that, compared with the single chamber measuring method requiring two successive steps of the volume increase and the establishing of equilibrium pressure following each, a two-chamber volume increase method may be implemented in virtually half the time required by the single chamber measuring method.

Here again it should be mentioned that the new devices equipped with at least one membrane as the volume-changing element need not be restricted to a two-step or multiple-step volume increase method.

A two-chamber variant comprising specifically different measuring chamber volume changes has proved advantageous particularly for implementing the new method, described above in the introduction, for determining the individual content quantities of more than one gas dissolved in a liquid.

An important requirement for routine measurements is that the time for establishing the equilibrium pressure after each volume increase is kept as short as possible, for which a motion-generating element, preferably an oscillating body, is used, which sets the sample liquid in cavitation-generating motion or oscillation.

An embodiment of the new device for determining the content quantities of gases dissolved in liquid and also the solubility (solubilities) and/or saturation pressure(s) thereof is particularly preferred. The special advantage of this embodiment of the device is that it can easily be fitted into a liquid vessel and/or a pipeline and in practice on-line or in-line measurements of the gas contents in the liquid, particularly a beverage, located in a vessel and/or flowing in a pipeline, may be undertaken.

This invention further includes various advantageous detailed development variants for the new device just described.

One embodiment avoids any direct connection between the sample liquid stirring element and the stirrer drive. Another embodiment variant has the advantage that only the sensor surfaces involved in active measurement come into contact with the sample liquid and the other regions or the data- and supply lines of the sensors are completely separate from the fluid space.

Another embodiment variant is advantageous and usable for on-line operation virtually without any limitations. It essentially comprises a sort of inverse embodiment to the on-line gas content measuring chamber.

Another aspect of the invention provides a measuring device for gases dissolved in liquids which is particularly simple as it does not have to be introduced directly into the sample liquid in a vessel or in a pipeline. The measuring chamber is here presented substantially as an extension in a bypass—parallel to a pipeline through which the liquid to be tested for its gas contents is flowing—wherein the closing of the measuring chamber is produced by respective valves in the bypass feed line to and discharge line from the measuring chamber. It may be advantageous with regard to this "bypass measuring chamber" arranged outside the pipeline to thermostat the chamber. Since the measuring chamber cannot be kept at a constant temperature by the liquid medium flowing round it, results can be obtained which are even more accurate than if the sample temperature is just measured in each case and taken into consideration in the calculation.

Here again the rotor or oscillating body serving to accelerate the establishing of the equilibrium pressure in the liquid to be measured can be separated from its drive by housing the drive in its own chamber.

With regard to the drive of the membrane, essential to the invention for the surface shape change and responsible for the volume change in the measuring chamber, the drive may operate in various ways.

A feature of the invention provides details of a type of control, preferred within the scope of the invention, of the mechanical components provided for opening and closing the measuring chamber when the sample is replaced.

Another aspect of the invention provides a mobile device for flexible use, substantially designed as a hand-operated instrument, for determining the content quantities of gases dissolved in liquids and their solubilities and/or their saturation pressures, it being necessary here to stress that a simplified bypass solution, i.e. a measuring chamber, which merely needs to be fitted fluid-tight to a connection issuing from a pipeline through which liquid is flowing, is particularly preferred, as in a measuring chamber of this kind the sample liquid no longer goes back into the pipeline or the vessel with the liquid after the measurement, but is discarded.

In a laboratory instrument, it may also be advantageous to thermostat the measuring chamber, e.g. with a Peltier thermostat. Thus in these laboratory applications in which the measuring chamber cannot be kept at a constant temperature by means of the liquid medium flowing round it, results can be obtained which are even more accurate than if the sample temperature is just measured in each case and taken into consideration in the calculation.

A further embodiment of the device according to the invention is particularly precise in its method of operation and space-savingly slim in its design. In this case the end or front surface of a very precisely guidable volume-changing piston substantially takes the place of a membrane, variable in its shape, as the partial region of the inside wall of the measuring chamber provided for changing the volume of the interior space thereof, which piston, sealed by means of an inherently stable seal to the inside wall of the measuring chamber preferably designed as a hollow cylinder, is movable therein so as to slide forward and back in a linear manner. The space-saving design is achieved by the fact that the rotor or stirrer for establishing the equilibrium in the measuring chamber and the drive providing for the rotation of the stirrer by means of a magnetic coupling through the end wall of the volume-changing piston are arranged one behind the other, as it were, and coaxially with the measuring chamber housing and with the measuring chamber. An important feature is also the mechanical control of the valves, operable by the volume-changing piston or upon the movement thereof, for supplying liquid for measuring into the measuring chamber and removing it therefrom after the completion of each measuring cycle.

A yet further embodiment of the invention is especially preferred, particularly with regard to maintaining a pressure of the sample liquid above the saturation pressure thereof to prevent bubble formation therein in the measuring chamber when the sample liquid is replaced between two measuring cycles or when the measuring chamber is filled before a new measuring cycle.

As far as the advantages of the new devices or device variants for analyzing gases dissolved in liquids are concerned, the following important points should be particularly emphasized:

The sample replacement and the establishing of the equilibrium pressure are able to take place quickly, and extrapolation of the equilibrium pressure is not necessary, with the result that very short measuring cycles with very high measuring accuracy are achieved.

The parts of the measuring chamber in contact with the sample may be designed so as to be smooth, self-emptying and without constrictions hindering automatic cleaning, so that the best hygiene preconditions for using these measuring devices in foodstuffs production are provided.

The number of moving parts and seals in the measuring devices is minimized, enabling lower production costs, high failure safety and long maintenance intervals to be achieved.

The devices according to the invention may be used for the greatest variety of applications and may be designed to comply with the particular requirements of each:

For use directly on a production line, thus on a pipeline in a beverage filling operation, for example, it may be designed as an "in-line instrument" which is flanged to the product line or to a product tank.

For use in a bypass configuration, a bypass instrument may easily be provided.

For the measurement on beverage casks and for spot-measurement on production lines, the new device may be designed as a portable, battery- and/or power-operated laboratory instrument, which may either be connected via hoses to the production line or with the aid of an appropriate filling means may be filled with the sample for measuring originating from a beverage cask in such a way that the content of dissolved gases in the sample liquid is not changed during filling, so that the measurement results remain unadulterated.

The device according to the invention in its variations differs substantially from instruments of the prior art known hitherto not only in that with the device the "two-step method" according to the invention for analyzing more than one gas dissolved in a liquid can easily be achieved, and optionally fully automatically if required, but also in the features which are advantageous when used in the method known per se with the purely "single expansion" of the measuring chamber volume. It can therefore be used both in accordance with the known method and also in particular in the various embodiments of the method according to the invention described above.

The invention is explained in detail with the aid of the drawing.

BRIEF DESCRIPTIONS OF THE DRAWINGS

Figure 2:
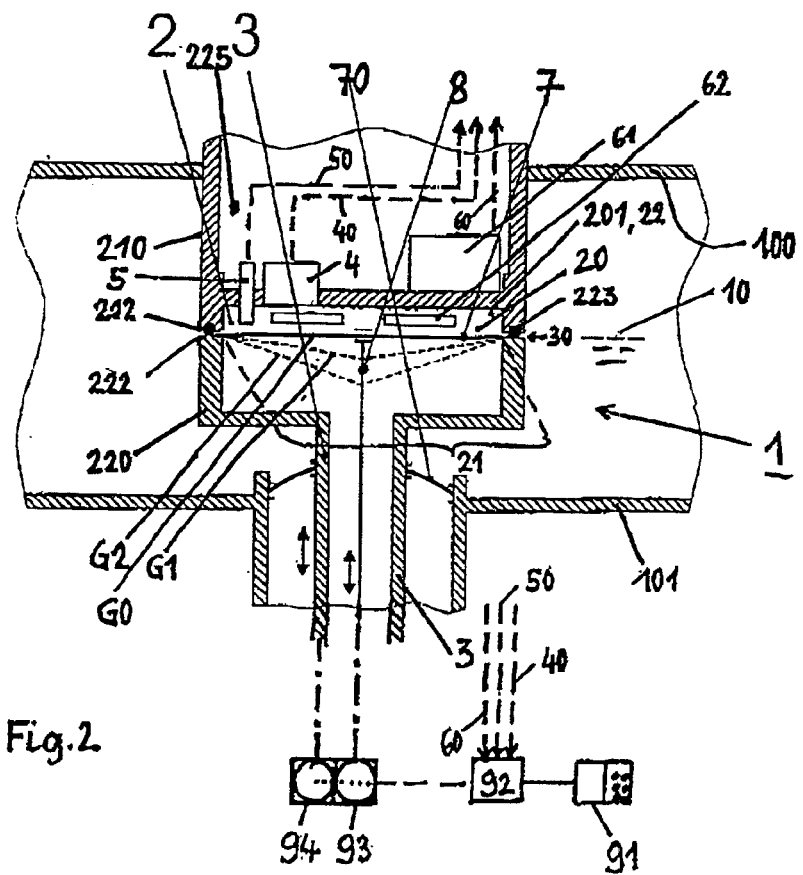
Figure 3:
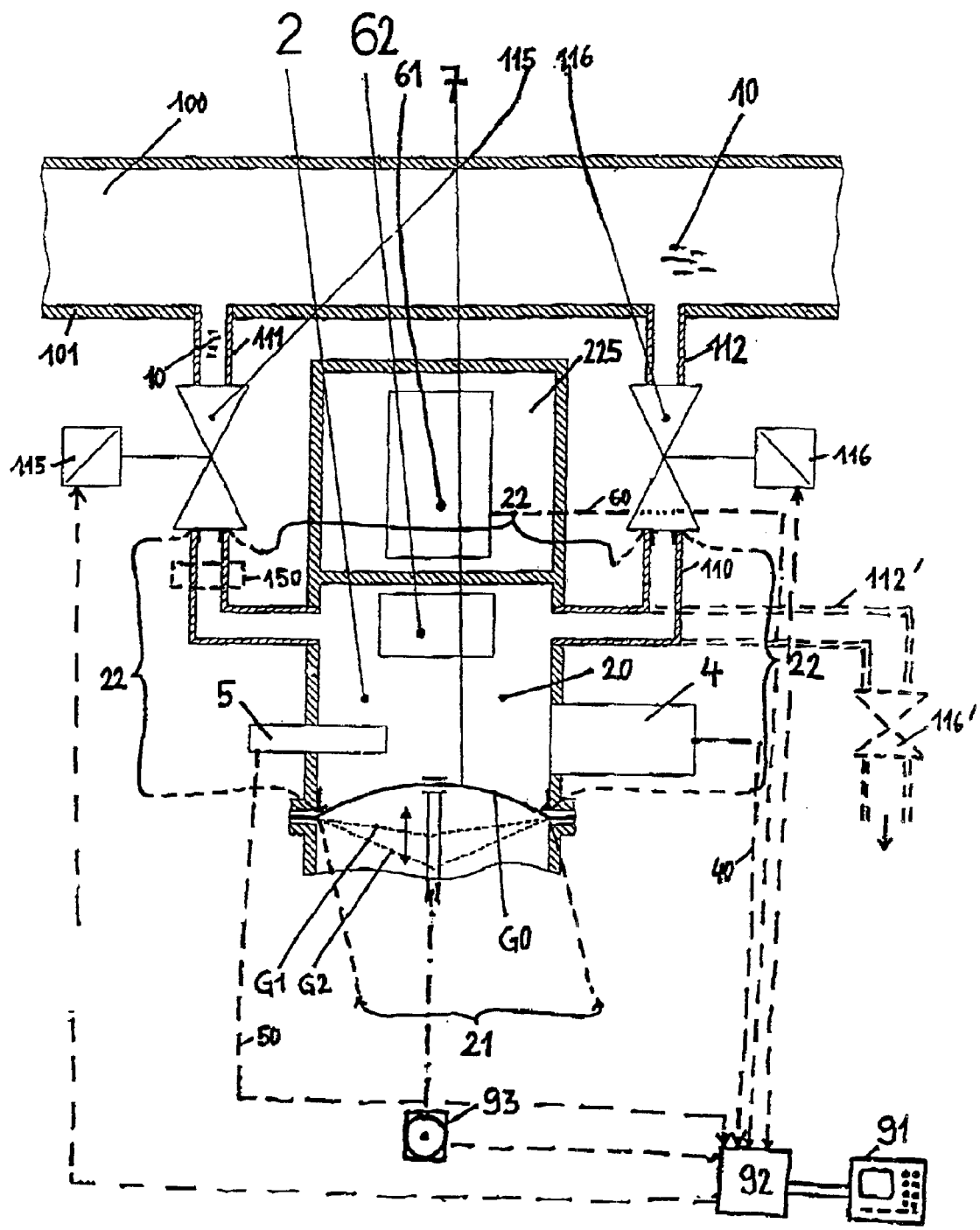
Figure 4:
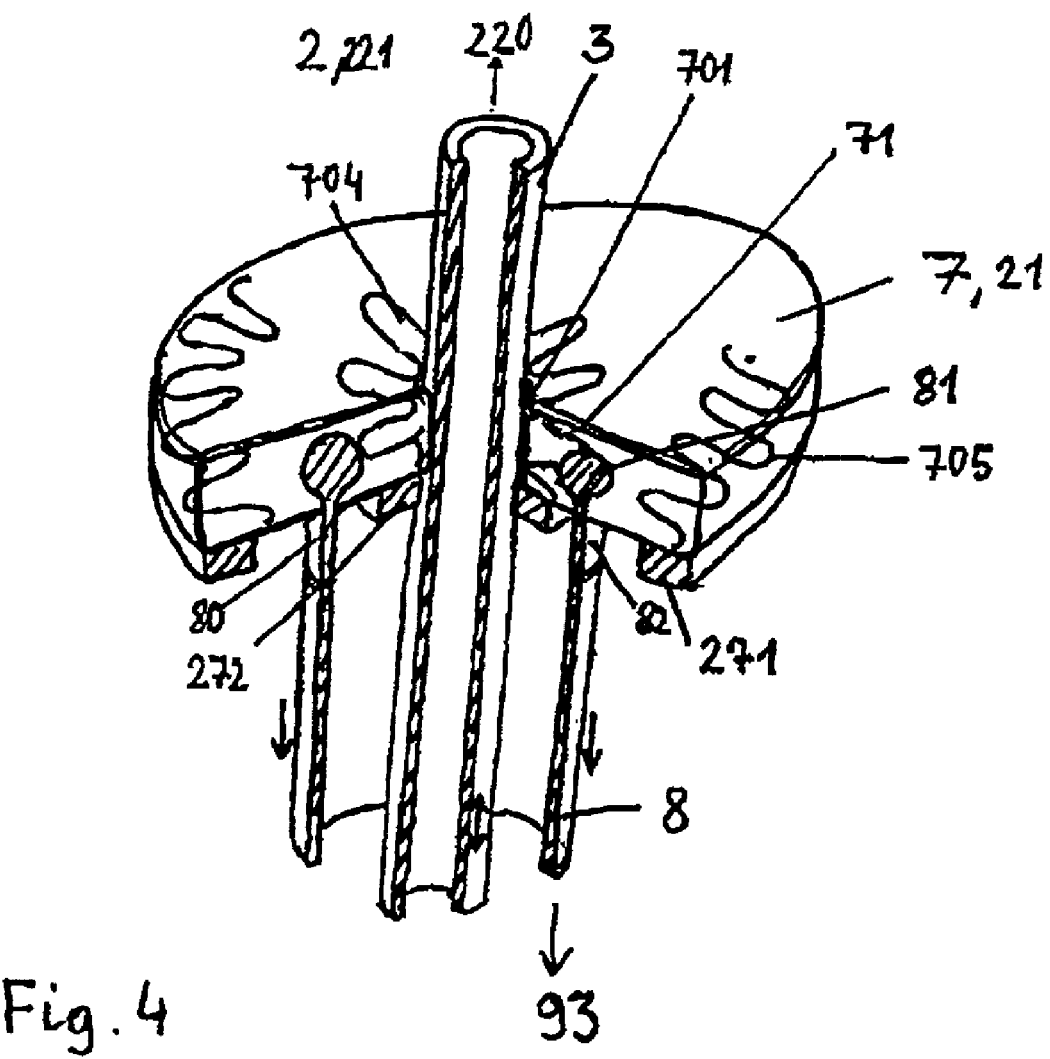
Figure 6:
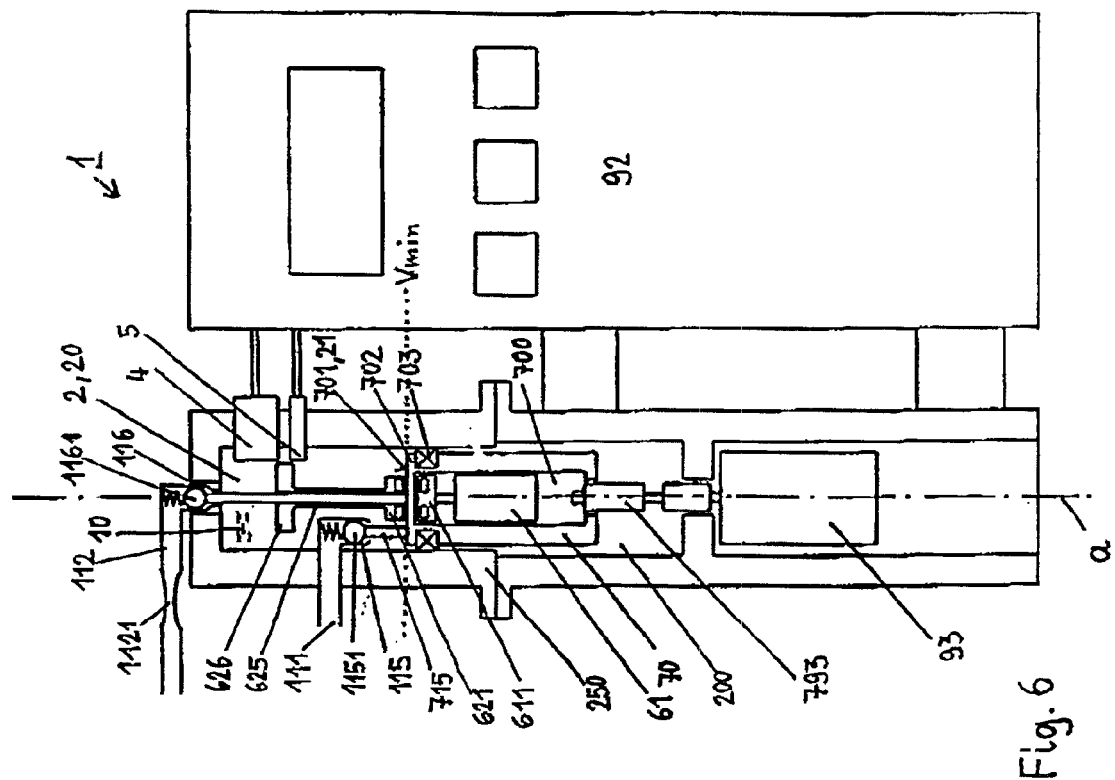
Figure 5:
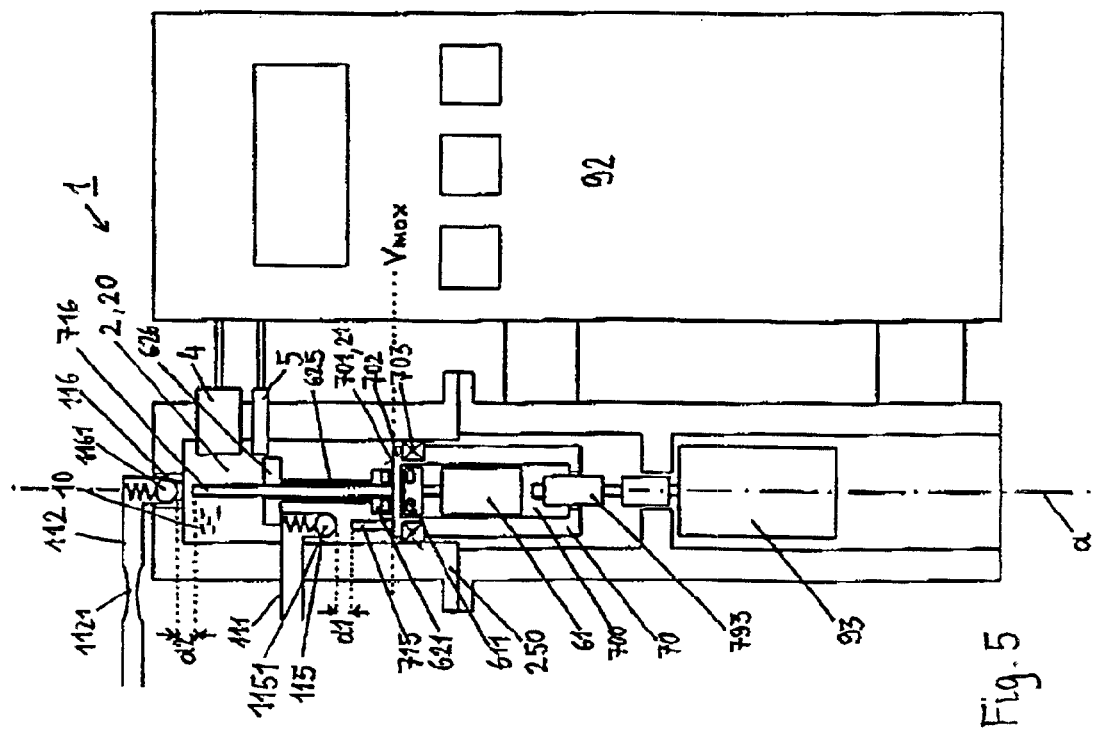

FIG. 1 shows in section an analyzer according to the invention on the single chamber principle, FIG. 2 shows in section an alternative embodiment on the single chamber principle, FIG. 3 shows in section a new analyzer designed as a bypass instrument, FIG. 4 is a diagram showing a part-sectional oblique view of the measuring chamber volume increase membrane, and FIGS. 5 and 6 show respective sectional views of another, particularly preferred embodiment of the new analyzer as a bypass instrument, in two different operating positions.

DESCRIPTION OF THE PREFERRED EMBODIMENTS

The embodiment of the new analyzer instrument 1 shown in FIG. 1 is formed with a housing connection 210 penetrating the wall 101 of a pipe 100 or vessel containing the liquid 10 for analysis and projecting into the sample liquid 10, the connection ending—upwardly in the drawing—with an annular edge 212 within which is arranged or stretched a membrane 7 made of an elastomeric material which adjoins the edge fluid-tight and is located in a plane-surface basic geometry G0. This membrane 7 may be changed in its surface shape or surface geometry in a defined manner and to a precisely predeterminable degree in each case by means of a rod-like or hollow cylinder-shape membrane driver 8, or several such drivers 8, secured to the membrane, by the movement thereof towards the exterior—or downwardly in FIG. 1.

In FIG. 1 two positions G1 and G2 of the membrane 7 are shown by a broken line, these positions corresponding to two defined surface geometries, other than the basic geometry G0, and chamber volume increases thereof.

Guided through the membrane 7, fluid-tight, is a hollow piston rod 3, by means of which a piston head 220 having a cavity 225 is movable upwardly in the direction away from the membrane 7, or in reverse. The piston 220 has an approximately flat cylinder-shape recess 201 directed towards the membrane 7 of the housing connection 210 and fully open towards the membrane, the annular edge 222 of the recess bearing a sealing ring 223 extending around it.

Into the recess 201 with its non-changeable interior wall 22 project the sensor parts or sensor surfaces of a pressure sensor 4 and a temperature sensor 5 proceeding from the piston cavity 225 and penetrating the partition 226 thereof separating it from the recess 201. The measured value transfer lines 40 and 50 of the sensors are guided, as is the power supply line 60 for the stirring element drive 61, out of the piston cavity 225 through the piston rod 3 to the exterior.

The analyzer 1 according to the invention is shown in FIG. 1 in a closed position enclosing the sample liquid 10 so as to effect a fluid-seal by means of the annular seal 223. In this closed position a measuring chamber 2 is formed with an interior space 20 having a defined standard measuring chamber volume, in which is located an oscillating element 62 operable in a non-contact manner by the aforementioned magnet-operated drive 61 in the piston cavity 225 to accelerate the establishing of equilibrium pressure.

In the measuring chamber 2 just defined, the membrane 7 forms a shape-variable region 21 of the wall of the chamber interior space, which may be converted in its shape or surface geometry from the basic geometry G0 into other surface shapes G1 or G2, the non-variable region 22 thereof being defined substantially by the internal wall of the recess 201.

When the surface geometry thereof is changed to the two geometries G1 and G2, for example, there occurs a first, smaller, increase in the volume of the measuring chamber interior space 20 and then a second, larger, such measuring chamber interior space volume increase.

After each of these volume increases—after appropriate cavitation-generating stirring by means of the oscillator 62, operable in a non-contact manner by means of the magnet-operated drive 61, to accelerate the establishing of the equilibrium pressure in the measuring chamber 2—as well as the temperature ascertained by means of the temperature-measuring probe 5, the equilibrium pressure established in the measuring chamber 2 is ascertained by means of the pressure-measuring probe 4. The measured pressure values obtained in this way form the basis for ascertaining the content quantities of dissolved gases in the sample liquid 10 and also the solubility (solubilities) and/or saturation pressure(s) thereof.

When the pressure measurements in the chamber 2 after at least two volume increases are completed, the piston 220 is moved—upwardly in the drawing—by means of the piston rod 3 and because of the creation of a slit-type opening 30 extending around between the edges 212 and 222, or the sealing body 223 located there, and opening of the measuring chamber 2 to its full extent results, bringing about the rapid and effective removal of the sample liquid 10 previously located therein and subjected to the volume increase steps, and the filling up thereof with the liquid 10 surrounding the measuring chamber 2, so that a new measuring cycle can be started very quickly.

To sum up and to explain in detail, the following should be emphasized:

The measuring chamber 2 is designed in the manner of a self-emptying box projecting into the liquid for measuring and with the liquid circulating around it, the box preferably being oriented not horizontally—as shown in the Figure—but vertically, which accelerates the flushing process even more.

The size of the opening gap 30 is such and the shape of the recess 201 of the measuring chamber 2 is designed such that the liquid sample for measurement is replaced in a very short time without any other assistance.

The piston rod 3 is guided in a leakage-free manner through the membrane 7 towards the exterior to a drive.

The membrane 7 may be resiliently extended additionally in a defined manner by means of a driver (drivers) 8, with the measuring chamber 2 closed, and may thus be changed in its surface geometry, thereby increasing the measuring chamber volume.

At the beginning of each measuring cycle, the measuring chamber 2 is opened by means of the piston rod 3. The sample liquid 10 in the measuring chamber 2 is replaced. The measuring chamber 2 is then sealed tight by withdrawing the piston rod 3.

The membrane 7 is extended by means of the membrane driver 8, by which the measuring chamber volume is increased and the sample liquid 10 in the measuring chamber 2 is expanded. The volume increase of the measuring chamber 2 may be set at a level such that any other dissolved gases present in the sample have only a minimal effect on the content thereafter to be determined in the liquid of a gas forming the main component, such as carbon dioxide.

The establishing of the equilibrium pressure inside the measuring chamber 2 is promoted by means of an oscillating body 62 whose rapid movement in the sample liquid 10 produces cavitation.

Alternatively, the degassing device for establishing the equilibrium pressure may consist of an ultrasonic transducer whose ultrasonic energy emitted therein is regulated such that the equilibrium pressure establishes quickly. The equilibrium pressure and the temperature are measured and from these the carbon dioxide content is calculated. Thereafter the membrane 7 is relaxed and by means of the piston rod 3 the measuring chamber 2 is opened.

In the gas content measuring device 1 shown in FIG. 1, according to the method of the invention, after a first determination of the equilibrium pressure and the temperature following a first volume increase in the chamber 2, by means of a second, further, extension of the membrane 7 by means of the driver 8, the measuring chamber volume is further increased, the degassing device 61, 62 is activated again and thereafter the changed equilibrium pressure newly established is determined. This process may also be run through several times.

Because of the effect of the differing solubilities of the gases dissolved in the sample liquid, from the measured equilibrium pressures it is possible, for instance, to eliminate the influence of the other dissolved gases on the ascertained carbon dioxide content by calculation and/or to determine the contents of the other dissolved gases, in particular oxygen and nitrogen, and the gas solubilities thereof as well.

According to an embodiment of the device according to the invention which is entirely analogous with regard to its structure, two or more measuring chambers 2 as just described, operated in parallel, may serve as measuring devices: in this case differing volume increases are implemented in each of the measuring chambers by means of differing changes of the shape of their membranes 7.

The separate pressure-measuring sensors 4 in multiple chambers of this kind are advantageously identical in design and the membranes 7 are adjustable to define volume increases which differ from one another in each case. With the aid of the differing equilibrium pressures then determined simultaneously in the measuring chambers 2, the effect of other dissolved gases, e.g. on the calculated carbon dioxide content, is eliminated by calculation, and/or the content quantities of the other dissolved gases and the gas solubilities and also saturation pressures can be determined as well.

In some—mostly more difficult—cases, it may also be advantageous to combine the device according to the invention with other sensors, preferably selective gas sensors, and to include their measured values in the result calculation based on the measured equilibrium pressure values.

FIG. 2 shows another embodiment of the invention—with reference numeral meanings otherwise unchanged or used analogously—which is particularly suitable for installation in pipelines. The piston rod 3 for opening and closing the measuring chamber 2 is in this case guided through the pipe wall 101 in a leakage-free manner via a membrane 70. Located in the hollow piston rod 3 is the membrane driver 8 which extends the membrane 7—the membrane here sealing off the piston 220 from the sample liquid 10 so as to effect a fluid-seal —by means of whose shape change the measuring chamber volume can be increased with the measuring chamber 2 closed.

In this embodiment according to FIG. 2 similar conditions substantially prevail as in the measuring device 1 according to FIG. 1, but here the recess 201 essential for forming the measuring chamber 2 or the interior space 20 thereof is arranged with its boundary wall region 22, which remains constant, in a housing connection 210 penetrating the wall 101 of the pipe 100 diametrically to the passage-through of the piston rod 3.

The connection 210 has a cavity 225—here open upwardly or towards the exterior—which is separated from the recess 201 by the partition 226. Located in the cavity are the measurement sensors 4, 5 for pressure and temperature which penetrate the partition 226 in a fluid-tight manner and whose actual sensor heads are in contact with the sample liquid 10 in the recess 201 or chamber 2, and also the non-contact magnet-operated drive 61 for the oscillating body 62.

When the membrane 7 forming the shape-variable region 21 of the measuring chamber boundary is moved upwardly with the piston 220, by means of the piston rod 3 by the drive 94 monitored by the control and calculation unit 92—the unit being adjustable from the input and display unit 91—the recess 201 with the sample liquid 10 located therein is closed fluid-tight and thus the measuring chamber 2 is formed with a precisely defined volume of the interior space 20.

Then, controlled by the control and calculation unit 92 on the basis of the parameters input via the input and display unit 91, there occur the volume increase steps and also the establishing of the equilibrium pressure, preferably accelerated by means of the oscillating body 62 operated in a non-contact manner by the magnet-operated drive 61 in the housing connection space 225, and thereafter the pressure and temperature measurement by means of the respective sensors 4 and 5, the measurement data of which are issued via the data lines 40 and 50 to the control and calculation unit 92 where, using an algorithm, as explained by way of example in the descriptive section, or one analogous thereto, they are converted into the required values of the content quantities of the dissolved gases, from the solubilities and/or saturation pressures thereof, and are passed to the input and display device 91 or alternatively straight to a control unit for the production line, i.e. a beverage production line, for example.

FIG. 3 shows—with otherwise analogous reference numeral meanings—a device according to the invention in the preferred embodiment as a bypass instrument. For practical reasons this is not directly fitted into the equipment, e.g. a pipeline 100, which contains the liquid 10 to be measured, but instead a partial flow of the liquid 10 to be analyzed is diverted from this equipment and supplied to the bypass instrument 1 where the measurement takes place. This partial flow is then returned or possibly discarded.

The feed and throughflow of the liquid 10 is achieved by opening the valves 115 and 116 located in the bypass feed line 111 and in the discharge line 112, whereby a previous liquid sample is flushed out.

Located in the measuring chamber 2 are a pressure sensor and a temperature sensor 4, 5, a degassing device 61, 62 provided according to the invention and the resilient membrane 7 provided for a specific measuring chamber volume increase and forming the shape-variable part 21 of the boundary wall of the measuring chamber interior space.

After the closing of the valves 115, 116, or of the measuring chamber 2, the membrane 7 is extended by means of the drive 93 and the driver 8 and the measuring chamber volume is thereby increased. The degassing device 61, 62 provided according to the invention steps into action and accelerates the establishing of the equilibrium pressure. The equilibrium pressure and the temperature are measured and from these the control and calculation unit 92 is able to calculate the content quantity (quantities) of dissolved gases, i.e. the carbon dioxide content, for example, of the liquid 10 for analysis.

According to the preferred embodiment of the invention, after the first volume increase and determining of the equilibrium pressure and the temperature, the measuring chamber volume is further increased, the degassing device 61, 62 is again activated and thereafter the newly established, now changed equilibrium pressure is again determined. This process can of course also be run through several times.

As a result of the effect of the differing solubilities of the gases dissolved in the sample liquid, it is possible from the measured values of the equilibrium pressures to eliminate the effect of the "other" dissolved gases, e.g. on the ascertained carbon dioxide content, by calculation and/or to determine the content quantities of the "other" dissolved gases, e.g. oxygen and nitrogen, and their solubilities in the sample liquid as well.

In this embodiment of the device according to the invention also, two or more bypass measuring chambers 2 may be used, operated in parallel and preferably equipped in the same way, the volume increases applied, in accordance with the method according to the invention, being adjusted in each of these measuring chambers to differing, respectively defined values.

With the aid of the differing equilibrium pressures determined simultaneously in the measuring chambers 2, the effect of the other dissolved gases on the calculated carbon dioxide content may be eliminated by calculation and/or the content of the other dissolved gases and/or their gas solubilities and/or saturation pressures may be determined as well.

Here too it may be advantageous to combine the device according to the invention with other sensors, preferably selective gas sensors, which may also be located entirely outside the measuring chamber, and to include the measured values delivered by the sensors in the result calculation.

With regard to the technical implementation itself, it should be emphasized quite generally at this point that the measuring device to be introduced into the liquid for measuring is advantageously equipped with connections or flanges which may be fitted to existing, normal industry-practice, standard connections or flanges or fittings of the vessels containing the liquid, tanks, or pipelines through which the liquid is flowing.

A device according to the invention for measuring the content quantities of dissolved gases on beverage casks and for spot-measurement on production lines or tanks may also be designed as a portable, battery- and/or power-operated laboratory instrument. This may either be attached to the production line 100 or to a product tank via hoses or may be filled from casks by means of a manual or automatic filling device.

A mobile analyzer instrument of this kind is represented in schematic form within the scope of FIG. 3, the instrument being attachable to a pipe connection 111, branching off the pipe 100 through which the liquid 10 is flowing and comprising a valve 115, e.g. by means of a pipe connection with a fluid-tight screw connection 150 or by means of a pressure-resistant hose via its feed line 111'; apart from the aforementioned connection 150 it has the same structure as the fixedly attached bypass instrument described above. Advantageously, however, there is no return into the main liquid stream provided, but there is an outlet pipe 112', closable for the measurement by means of a valve 116'—illustrated in this particular case by a broken line—by means of which the sample liquid 10 may be disposed of after the measurements have taken place.

The membrane 7 shown in FIG. 4 and variable in its surface geometry forms the part 21 of the boundary wall of the measuring chamber which is variable in its shape. This membrane 7 is made of a relatively thick (e.g. 5 mm) heavy-duty elastomeric material, such as Perbunan, for example, and has on its side directed towards the measuring chamber interior space an adhesion-reducing, hydrophobic coating 71 made of Teflon, for example.

On its outside periphery the membrane is held by a fixed membrane stop or membrane-supporting ring 271 joined to the measuring chamber housing, for example, or is clamped therein.

Centrally the membrane 7 has an opening 701 which is penetrated by the piston rod 3, as shown in FIG. 1, for the movement of the piston head 220 shown therein, comprising the recess 201—there forming the non-variable part of the measuring chamber 2.

The inside edge of the elastomeric membrane 7 encircling this passage opening 701 is joined to a membrane-supporting ring 272 which supports or holds the membrane at that location, is joined to the piston rod 3 and, with the measuring chamber closed, is therefore stationary and specifically positioned.

Vulcanized into the membrane 7 is the thickened edge 81 of a securing ring 80, projecting from the underside of the membrane 7, which is joined, for instance, to a hollow operating rod 8 designed to cooperate with the downwardly protruding part 82 of the ring 80, or to a hollow cylinder of that kind, which rod or cylinder is joined to the membrane-operating drive 93 provided for defined shape-changing of the membrane 7 and shown in FIG. 2, for instance. The membrane 7 may be flat, for example, in the basic position shown in FIG. 4 corresponding to the standard volume of the measuring chamber, and as the membrane operating hollow cylinder 8 moves downwardly to effect a desired increase in the interior space volume of the measuring chamber, it then forms a sort of circularly closed, flat-V-shape valley.

Also indicated in FIG. 4 is how the membrane 7 or the inside and outside edge regions thereof are provided at that location with meander-shape or toothed reinforcing structures 704, 705 joined to the membrane or supporting it, which structures serve to ensure the geometrically true shape and also the defined shape change of the membrane 7 supported over a large area thereon even after a large number of measurements with volume increase steps.

FIGS. 5 and 6 show—with reference numeral meanings otherwise unchanged—sections through another, particularly preferred embodiment of the new measuring device 1 comprising a measuring chamber 2, wherein the front surface 701 of a hollow volume-changing piston 70 is substantially provided as the movable wall region 21 changing the volume of the interior space 20 of the measuring chamber 2, the piston being movable so as to slide in a linear manner in the interior or cavity 200 of the housing 250 accommodating the measuring chamber 2.

FIG. 5 shows the measuring chamber 2 in the state of having the maximum interior space volume, in which the volume-changing piston 70 occupies a "bottommost" position Vmax, and the valve bodies 1151, 1161, acted upon with the force of respective springs, of the inlet valve 115 in the feed line 111 of the measuring bypass and the outlet valve 116 in the discharge line 112 of the bypass, the bypass being connectible or connected to a pipeline—not shown—with the sample liquid 10 to be tested for its gas content flowing through the pipeline, are seated in their valve seats so as to effect a fluid-seal, and thus both valves 115, 116 are held closed.

The volume-changing piston 70 is sealed, by means of an inherently stable sealing ring 703 preferably made of an inert material such as Teflon in particular, against the inside wall of the housing cavity 200, or the measuring chamber 2, so as to effect a sliding seal. The drive of the volume-changing piston 70 is effected by means of a motor 93 with a linear drive such as a spindle drive 793, which motor is controlled from the control and calculation unit 92 and is arranged in the cavity 200 of the housing 250 in line with the housing axis.

Located in the interior or cavity 700 of the piston 70 is a stirrer drive motor 61—again arranged in line with the axis a of the housing 250—with a disc-type magnetic body 611, the magnets thereof—acting through the end wall 702 of the volume-changing piston 70—being magnetic force-coupled with the magnets of the similarly disc-type magnetic body 621 of a rotor or stirrer 62 arranged in the measuring chamber 2, or in the interior space 20 thereof, again in line with the housing axis. The rotor or stirrer arms or blades 626 are arranged on a hollow stirrer shaft 625, projecting upwardly from the magnetic body 621, at a distance away from the magnetic body 621.

Two valve control rods 715 and 716 project upwardly from the end wall 702 or out of the end surface 701 of the volume-changing piston 70 parallel to or in line with the housing axis a, the control rod 716 passing through the hollow stirrer 62.

In the illustrated end position Vmax of the volume-changing piston 70—which corresponds to the maximum volume of the interior space 20 of the measuring chamber 2 adjustable in the measuring chamber—the ends of the two valve control rods 715, 716 are located relatively far away from the spring-loaded valve bodies 1151, 1161—here in the form of ball valves—of the sample liquid inlet valve 115 located in the feed line 111 opening into the measuring chamber 2 for the sample liquid 10 to be tested for its content of dissolved gases, and of the outlet valve 116 located in the discharge line 112—leading out of the measuring chamber 2.

The distance d2 marked in FIG. 5 between the free end of the valve control rod 716 and the valve body 1161 of the outlet valve 116 is slightly smaller than the maximum clearance of the movement of the volume-changing piston 70, whose task is to be available for the step-by-step increase of the volume of the measuring chamber interior space 20 provided during the individual measurements in the course of a measuring cycle.

The distances d1 and d2 between the ends of the valve control rods 715 and 716 and the valve bodies 1151 and 1161 are advantageously such that, after the opening of the valves 115 and 116 when the measuring chamber 2 is filled with fresh sample liquid 10 before the commencement of a measuring cycle, as the volume-hanging piston 70 moves away from the valves 115 and 116, i.e. when the in- and outflow 111, 112 of sample liquid 10 into or out of the measuring chamber 2 is stopped, the outlet valve 116 is closed earlier than the inlet valve 115.

Also to be inferred from FIG. 5—indicated by means of a constriction of the discharge line 112—is a pressure-reducing element 1121, or pressure-reducing valve, which serves to adjust the throughflow of the sample liquid, more particularly when the sample liquid is replaced, such that the pressure of the sample liquid 10 does not fall below the saturation pressure thereof during filling, so ensuring gas bubble-free filling of the measuring chamber 2.

FIG. 6 shows—with reference numeral meanings fully analogous to FIG. 5—the state of the new measuring device 1 during replacement of the sample liquid 10 to be tested for its gas content after completion of one measuring cycle and before the commencement of a new measuring cycle.

Here, the volume-changing piston 70 is located in an "upper" end position Vmin, in which the variable volume of the interior space 20 of the measuring chamber 2 is at its smallest. The two valve control rods 715, 716 have in this case lifted the valve bodies 1151 and 1161, against the force of the valve springs thereof, off the seats of the valves 115 and 116, so that the previously tested sample liquid 10 is able to flow out of the measuring chamber 2 and fresh sample liquid is able to flow in. As already stated above, by means of a pressure-reducing element or restrictor 1121 in the discharge line 112, the pressure in the sample liquid 10 may be kept at a pressure above the saturation pressure thereof, and in this way the formation of bubbles of the dissolved gas is prevented.

What is claimed is:

1. A method for selectively determining the quantities of at least two of a plurality of gases dissolved in a liquid, which gases differ from one another in their solubilities, comprising:
    completely filling a measuring chamber with a sample of the liquid to be tested and equipping the measuring chamber with a pressure measuring sensor;
    closing the measuring chamber in a fluid-tight manner, thereby defining a standard measuring chamber volume;
    increasing the volume of the closed measuring chamber in a number of steps corresponding at least to the number of gases whose quantities are to be determined by volume increase factors which, related to the standard chamber volume, differ from one another,
    after each of the volume increase steps, determining an equilibrium pressure then established in the measuring chamber; and
    on the basis of the determined equilibrium pressures, calculating the quantities of the at least two gases in the liquid sample.

2. A method according to claim 1 wherein each step of increasing the volume of the measuring chamber filled with the liquid sample comprises, starting from the standard chamber volume, increasing the volume by a factor ranging from 1.005 to 1.75.

3. A method according to claim 1 wherein by means of a temperature-measuring sensor arranged in the measuring chamber a temperature of the liquid sample is ascertained, and including the measured temperature of the liquid sample in the calculation of the content quantities of the at least two gases dissolved in the liquid.

4. A method according to claim 1 wherein increasing the volume of the measuring chamber in a number of steps occurs sequentially in one and the same measuring chamber filled with the liquid sample, wherein after each volume increasing step the equilibrium pressure in the measuring chamber is determined, and using the determined equilibrium pressures to calculate the quantities of the at least two gases in the liquid sample.

5. A method according to claim 1 including providing at least two measuring chambers, wherein the number of steps of increasing are implemented in the at least two measuring chambers each filled with the liquid sample, and thereafter determining the equilibrium pressure established in each of the measuring chambers, and using the equilibrium pressures to calculate the content quantities of the at least two gases in the liquid sample.

6. A method according to claim 1 comprising completely filling a single measuring chamber, and wherein the number of steps of increasing occur in chronological succession with the volume increase factors increasing with each of the increasing steps.

7. A method according to claim 1 wherein the step of increasing the measuring chamber volume is performed a number of times which equals the number of gases dissolved in the liquid having a solubility or content quantity which is not to be disregarded.

8. A method according to claim 1 wherein $CO_2$ is dissolved in the liquid sample as a main component, and wherein oxygen and nitrogen also dissolved in the liquid sample in smaller quantities are treated as a unified double gas component having a mean solubility.

9. A method according to claim 1 wherein increasing the measuring chamber volume comprises providing a membrane forming a partial region of a boundary of the measuring chamber, and changing a shape of the membrane.

10. A method according to claim 1 including providing a selective gas sensor in contact with the liquid sample and including an output of the selective gas sensor in calculating the quantities of the at least two gases in the liquid sample.

11. A method according to claim 1 including subjecting the liquid sample to rapid, cavitation generating movement in order to accelerate establishing the equilibrium pressure in the measuring chamber.

12. A method according to claim 11 wherein subjecting the liquid sample to movement comprises subjecting the liquid sample to at least one of oscillations and rotation.

13. A method according to claim 11 including accelerating establishing the equilibrium pressure by subjecting the liquid sample to cavitation by means of an ultrasonic transducer equipped with a regulating device for power introduced into the liquid sample.

14. A method according to claim 13 including using the pressure measured in the measuring chamber after the ultrasonic transducer has been switched off as a regulating variable for ultrasonic power to be introduced into the liquid sample.

15. A device for quantitatively determining the presence of at least two gases dissolved in a liquid by filling a measuring chamber with a sample of the liquid to be tested, closing the measuring chamber in a fluid-tight manner to define a standard measuring chamber volume, increasing the volume of the closed measuring chamber in a number of steps corresponding at least to the number of gases whose quantities are to be determined by volume increase factors which, related to the standard chamber volume, differ from one another, after each of the volume increase steps, determining an equilibrium pressure then established in the measuring chamber, and on the basis of the determined pressures, calculating the quantities of at least two of the gases in the liquid sample, the device comprising a fluid-tight measuring chamber having an interior space which can be filled completely with the liquid sample and closed fluid-tight so that the chamber defines the standard chamber volume, a membrane defining at least one partial region of a boundary of the interior space, and a drive element for changing the volume of the interior space by varying at least one of a position and surface geometry of the membrane in a number of discrete steps which produces corresponding increases in the volume of the measuring chamber interior space and thereby of the standard chamber volume corresponding to a freely selectable and adjustable volume increase factor.

16. A device according to claim 15 comprising at least two measuring chambers adapted for filling completely with the liquid sample and closable fluid-tight, each measuring chamber comprising at least one partial region of the boundary of its respective interior space for changing the volume of the interior space by varying at least one of the position and surface geometry of the membrane, the membrane being movable into or deformable to at least one defined location position or surface geometry which produces an increase in the volume of the measuring chamber interior space and thereby of the standard chamber volume corresponding to a freely selectable and adjustable volume increase factor.

17. A device according to claim 16 wherein, in order selectively to determine the quantities of the at least two gases dissolved in the liquid, the membrane of each measuring chamber is movable relative to or deformable to produce increases in the volume of the interior space of the measuring chamber and thereby of the standard chamber volume corresponding to respective, differing volume increase factors.

18. A device according to claim 15 including at least one motion-generating element which sets the liquid sample in motion or subjects it to cavitation for accelerating establishing the equilibrium pressure.

19. A device according to claim 15 including a drive element for varying the at least one of the position and the surface geometry of the membrane, and a control and calculation unit controlling the drive element and generating a desired measuring chamber volume increase factor.

20. A device according to claim 15 wherein the liquid is in one of a vessel and a flow conduit, each having a wall, wherein the measuring chamber projects through the wall into the liquid, wherein the at least one partial region formed by the membrane is variable in its surface geometry in a reproducibly defined manner by means of at least one membrane driver and a drive element coupled thereto and which closes off on a liquid side a wall connection and penetrates the wall in a fluid-tight manner, wherein another partial region is formed substantially by an inside surface of a recess which is open towards the membrane, and has an edge and a ring-shaped sealing body therein in the shape of one of a flat cylinder and a flat indentation for holding the liquid sample, wherein the recess is formed on a housing piston which is movable by means of a piston rod penetrating the membrane in a fluid-tight manner to open the measuring chamber interior space and to fill the interior space with the liquid sample away from the membrane to thereby free an opening slit extending around between the housing connection with the membrane, or the edge thereof, and the sealing body, and back in a direction towards the membrane to enclose the liquid sample in the measuring chamber interior space in a fluid-tight manner.

21. A device according to claim 20 wherein the housing piston has a fluid-tight cavity, separated from the recess, in which there is arranged a magnet-operated induction drive element for at least one of an oscillating body and a rotational body in the measuring chamber interior space for accelerating establishing equilibrium pressure in the measuring chamber filled with the liquid sample.

22. A device according to claim 21 including a partition between the measuring chamber recess and the cavity of the housing piston fitted with a pressure-measuring sensor extending into the measuring chamber or in contact with the liquid sample enclosed therein.

23. A device according to claim 22 including measurement data lines coupled with the sensor and power supply and control lines coupled with a drive element of the oscillating or rotational body guided through the cavity of the housing piston and through the interior space or through a cavity of the piston rod thereof to the exterior.

24. A device according to claim 15 wherein the liquid is in one of a vessel and a flow conduit, each having a wall, and wherein a partial region of the boundary of the measuring chamber is formed by a recess of a pipe or housing connection penetrating the wall in a fluid-tight manner and closed off towards the exterior by a partition, the recess being open to the liquid when the chamber is filled and having a ring-shaped sealing body on its edges, a remaining partial region of the measuring chamber interior space boundary being formed by a membrane directed towards the recess of the connection and variable in its surface geometry by means of a membrane driver, a liquid side of the membrane sealing a hollow housing piston which is movable by means of a hollow piston rod guided through a fluid-sealing passage formed with a membrane in the wall, the housing piston with the membrane being movable away from the recess of the connection to open and fill the measuring chamber, and to free a slit opening extending around between the sealing body of the housing connection and the edge of the housing piston sealed by the membrane, and being movable back in the direction towards the recess of the connection to close the measuring chamber.

25. A device according to claim 15 wherein the measuring chamber comprises a bypass line branching off the conduit through which the liquid for analysis is flowing and leading back and having closable closing elements including valves in a feed portion of the bypass line to the measuring chamber and in a discharge portion of the bypass line from the measuring chamber, and wherein a partial region of the boundary of the interior space of the measuring chamber is formed by a membrane which is variable in its surface geometry in a defined manner by means of a membrane driver.

26. A device according to claim 24 including a magnet-operated induction drive element arranged in a space separated from the measuring chamber by a partition, and at least one of an oscillating body and a rotor body located in the measuring chamber and driven by the drive element for establishing the equilibrium pressure.

27. A device according to claim 15 wherein the drive element comprises one of a stepping motor and a pneumatic drive, the drive element being controllable via a control and calculation device for the input of a desired volume increase factor.

28. A device according to claim 15 wherein the drive element is controllable via a control and calculation device from an input and display device for the input of one of a desired flushing time and equilibrium pressure establishing time.

29. A device according to claim 15 configured as a hand-operated analyzer instrument having an input, a display, a control and a calculation device and wherein the drive element is fed by a power store, the instrument being adapted for introducing into a liquid for analysis of its content of dissolved gases.

30. A device according to claim 29 wherein the measuring chamber has a feed line connectible fluid-tight to a conduit through which the liquid is flowing, and a liquid outlet line comprising a closing valve.

31. A device according to claim 15 wherein
the measuring chamber is equipped with a feed line for the liquid sample and comprising a stop valve and a discharge line comprising a stop valve arranged in an elongated tubular housing,
wherein, for changing the volume of the interior space, an end surface of a volume-changing piston is provided, the end surface forming a partial region of a wall of the measuring chamber interior space, the piston being sealed in a cavity of a housing against an inside wall of the housing cavity or of the measuring chamber by means of a seal that is movable so as to slide, effecting a fluid seal that is hollow,
the piston being movable in a linear manner via one of a linear spindle drive and a drive motor arranged in line with an axis of the housing and operable, controllable and regulatable from a control unit, and
wherein a rotor or stirrer drive comprising a magnetic body is arranged in the cavity of the volume-changing piston coaxially with an axis of the housing, the magnetic body being magnetically force-coupled in a non-contact manner through an end wall of the volume-changing piston with a magnetic body of a rotor/stirrer arranged so as to be coaxial with the housing axis and including stirrer arms located at a distance from the magnetic body on a hollow stirrer shaft,
wherein from the end surface of the volume-changing piston there project two valve control rods oriented substantially parallel to the housing axis, one of the control rods being coaxial with the housing axis and passing through the cavity of the stirrer,
by means of which the valves of the feed and discharge lines can be opened by lifting of associated spring force-operated valve bodies off the sealing seat, the distances between the valve control rod and the valve body of the inlet valve and the valve control rod and the valve body of the outlet valve being dimensioned such that when the measuring chamber is filled with liquid sample at the beginning of a measuring cycle and as the volume-changing piston moves away from the valves, the outlet valve is closed before the inlet valve is closed.

32. A device according to claim 31 including one of a throughflow-regulating valve and a pressure-reducing valve arranged in the discharge line for maintaining the pressure in the liquid sample above a saturation pressure of the liquid sample.

33. A method according to claim 1 wherein calculating includes calculating at least one of a solubility and a saturation pressure of at least one of the at least two gases.

34. A method according to claim 2 wherein the factor is in a range between 1.01 and 1.50.

35. A method according to claim 2 wherein the factor is in a range of between 1.03 to 1.10.

36. A method according to claim 12 wherein subjecting the liquid sample to at least one of oscillations and rotation comprises placing an oscillating body and a rotor, respectively, in the liquid sample.

37. A method according to claim 36 including magnetically coupling the rotor with a rotational drive.

38. A device according to claim 16 wherein the at least two measuring chambers are identically configured.

39. A device according to claim 18 including a drive for the motion generating element, and a magnetic coupling operatively connecting the drive and the motion generating element.

40. A device according to claim 22 including a temperature measuring sensor extending into the measuring chamber.

41. A device according to claim 29 wherein the hand-operated analyzer instrument has the approximate form of a dip-stick.

42. A device according to claim 29 including a bypass line from the conduit to the measuring chamber, and wherein the hand-operator analyzer instrument is attachable externally to the bypass line.

43. A device according to claim 29 wherein the hand-operated analyzer instrument includes a thermostat for controlling the temperature of the liquid sample.

* * * * *